United States Patent
Dunhao et al.

(10) Patent No.: US 6,694,973 B1
(45) Date of Patent: Feb. 24, 2004

(54) NASAL MASK FOR USE IN INTERMITTENT POSITIVE PRESSURE VENTILATION THERAPY

(75) Inventors: Chen Dunhao, Iwakuni (JP); Ken Imai, Hino (JP); Shinichi Tao, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/496,650

(22) Filed: Feb. 3, 2000

(30) Foreign Application Priority Data

Feb. 4, 1999 (JP) .......................................... 11-027734

(51) Int. Cl.[7] ............................................ A61M 16/10
(52) U.S. Cl. ............................ 128/203.12; 128/205.25; 128/206.21
(58) Field of Search ................... 128/200.14, 200.24, 128/203.12, 203.14, 203.16, 203.22, 203.25, 203.29, 204.18, 205.24, 205.25, 206.2–207.18

(56) References Cited

U.S. PATENT DOCUMENTS

| 2,931,356 A | * | 4/1960 | Schwarz ................ 128/206.24 |
| 3,977,432 A | | 8/1976 | Vidal |
| 4,274,406 A | | 6/1981 | Bartholomew |
| 4,649,912 A | * | 3/1987 | Collins .................. 128/202.13 |
| 4,706,683 A | * | 11/1987 | Chilton et al. ......... 128/203.12 |
| 4,971,051 A | | 11/1990 | Toffolon |
| 5,485,827 A | * | 1/1996 | Zapol et al. ........... 128/200.14 |
| 5,586,551 A | * | 12/1996 | Hilliard ................. 128/203.29 |
| 5,839,433 A | * | 11/1998 | Higenbottam .......... 128/204.21 |
| 6,357,437 B1 | * | 3/2002 | Jacques ................. 128/201.25 |

FOREIGN PATENT DOCUMENTS

| FR | 2-735-030 A1 | 12/1996 |
| WO | WO 98/34665 | 8/1998 |

* cited by examiner

*Primary Examiner*—Glenn K. Dawson
(74) *Attorney, Agent, or Firm*—Sughrue Mion, PLLC

(57) ABSTRACT

A nasal mask for use with a system for supplying air with a therapeutic gas to the airways of a patient includes a mask shell which is adapted to be put over the nose of the patient using the nasal mask; an air inlet port through which air is supplied from an air source; an exhaust port, provided in the mask shell, for discharging the exhalation gas to atmosphere; and a therapeutic gas inlet port, provided on the mask shell adjacent to the exhaust port. The therapeutic gas port is fluidly connected to a therapeutic gas source which supplies a therapeutic gas at a constant flow rate. The therapeutic gas port is oriented toward a portion of the inside volume of the nasal mask over the nose of the face of the patient using the nasal mask.

6 Claims, 5 Drawing Sheets

NASAL MASK FOR USE IN INTERMITTENT POSITIVE PRESSURE VENTILATION THERAPY

BACKGROUND OF THE INVENTION

1. Field of the Invention

The invention relates to a nasal mask for use with an intermittent positive pressure ventilation system for introducing a therapeutic gas, such as oxygen or nitrogen monoxide into the lungs of a patient.

2. Description of the Related Art

An intermittent positive pressure ventilation system is generally used for supporting a ventilatory insufficiency patient. FIG. 8 shows a nasal mask 100 of a prior art which includes a mask shell 102 and a flexible cushion 104 which is detachably attached to the mask shell 102. The mask shell 102 is fluidly connected to an air source 112 through an air conduit 106. The air source supplies air to the mask 100 alternately at high pressure, for example at 20 cm $H_2O$, referred to inhalation pressure, and at low pressure, for example at 4 cm $H_2O$, referred to exhalation pressure. An exhaust port 110 is provided in the air conduit 106 for discharging the exhalation gas from the patient using this nasal mask 100.

A therapeutic gas inlet port 108 is provided in the mask shell 102 which is fluidly connected to a therapeutic gas source (not shown) by a tube (not shown).

The therapeutic gas inlet port 108 is oriented to a region Rn within the nasal mask 100 under the nose of the patient using this nasal mask 100.

With the nasal mask 100 of FIG. 8, a large portion of the inside volume of the nasal mask 100, except for the region Rn under the nose of the patient, is filled with the exhalation gas from the patient, which includes carbon dioxide gas at high concentration, just before the initiation of the inhalation phase of the next breathing cycle because the exhaust port 110 is provided on the air conduit 106 away from the nose of the patient. Therefore, the patient will draw the exhaled gas in again. This increases the carbon dioxide concentration in the blood of the patient using the nasal mask 100 of the prior art.

On the other hand, in the region Rn under the nose within the nasal mask 100, an oxygen rich space is generated just before the initiation of the inhalation phase of the next breathing cycle, since the oxygen gas inlet port 108 is oriented to the region Rn and the flow rate of the exhalation gas from the nose decrease substantially to zero at the end of the exhalation phase. The volume of the oxygen rich space depends on the magnitude of the breathing and the higher the magnitude, the smaller the volume of the oxygen rich space produced in the region Rn under the nose. The volume of the oxygen rich space also depends on the flow rate of the oxygen gas supplied through the therapeutic gas inlet port 108 and the higher the flow rate, the larger the volume of the oxygen rich space produced. This will be a problem when the patient sleeps because the patient will draw an inhalation gas of high oxygen concentration, which results in depression of the respiratory center to further decrease the breathing.

Another nasal mask is disclosed in WO 98/34665 which includes an exhaust port provided in the mask shell and a therapeutic gas inlet port provided on the air conduit for supplying air. The configuration of the nasal mask can substantially avoid or reduce the above-described problems.

However, the nasal mask of WO 98/34665 involves another problem that the most of the oxygen gas supplied to the mask during the exhalation phase is entrained into the air flow through the air conduit and discharged through the exhaust port without being used. Further, with the nasal mask of WO 98/34665, a very large amount of oxygen is required in order to increase the peak of the oxygen concentration in the inhalation gas which the patient draws during the inhalation phase.

SUMMARY OF THE INVENTION

The invention is directed to solve the prior art problems, and to provide an improved nasal mask which provides a high peak therapeutic gas concentration in the inhalation gas and reduces carbon dioxide rebreathing.

According to the invention there is provided a nasal mask, for use with a system for supplying air with a therapeutic gas to the airways of a patient, which includes a mask shell which is adapted to be put over the nose of the patient using the nasal mask; an air inlet port through which air is supplied from an air source; an exhaust port, provided in the mask shell, for discharging the exhalation gas to atmosphere; and a therapeutic gas inlet port, provided on the mask shell adjacent to the exhaust port. The therapeutic gas port is fluidly connected to a therapeutic gas source which supplies a therapeutic gas at a constant flow rate. The therapeutic gas port is oriented toward a portion of the inside volume of the nasal mask over the nose of the face of the patient using the nasal mask.

DESCRIPTION OF THE DRAWINGS

These and other objects and advantages, and a further description, will now be discussed in connection with the drawings in which.

DESCRIPTION OF THE PREFERRED EMBODIMENTS

Figure 1:
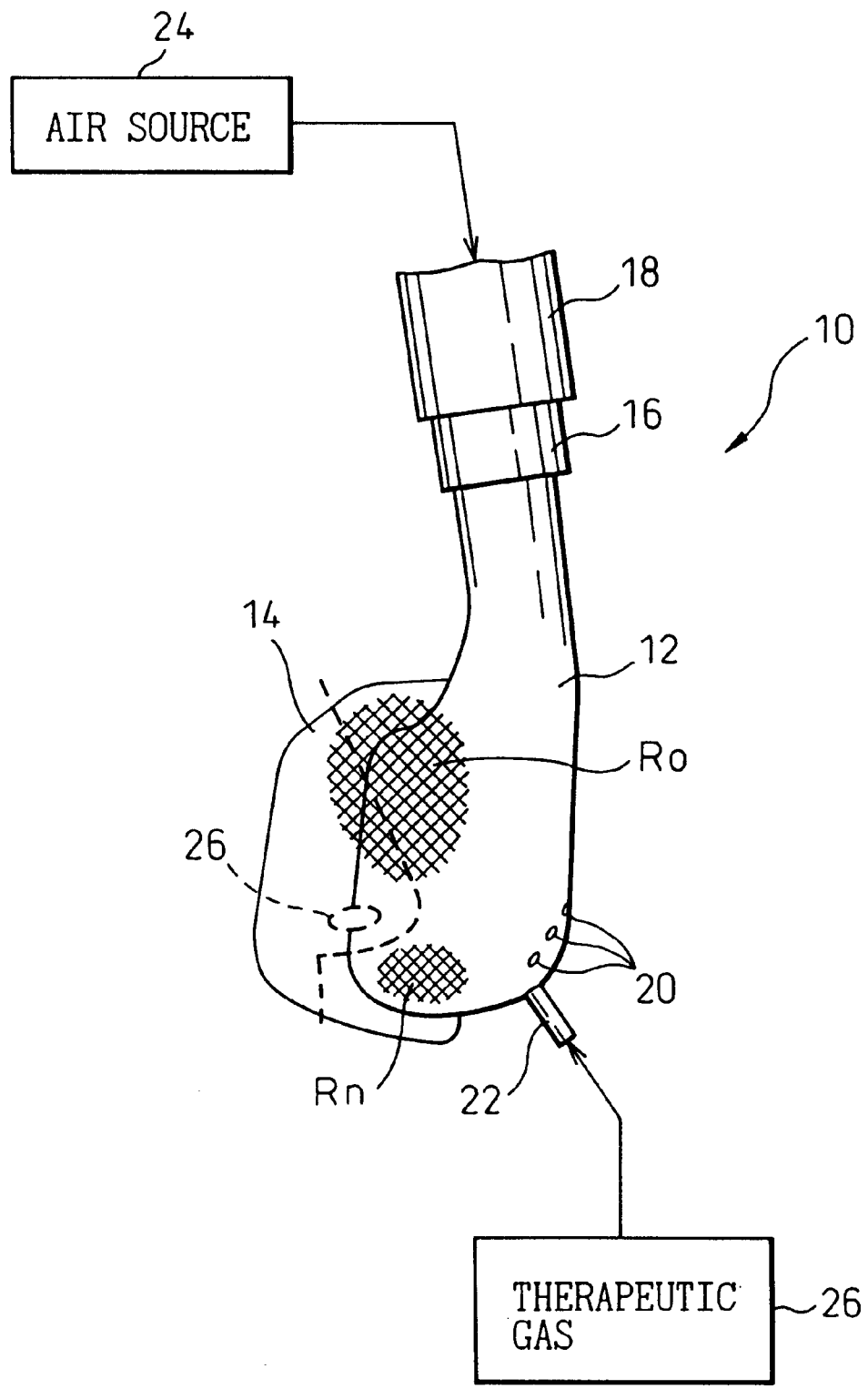
FIG. 1 is schematic side view of a nasal mask according to a preferred embodiment of the invention, the nasal mask being put on the face of a patient.

With reference to FIGS. 1 to 4, a nasal mask according to the preferred embodiment of the invention will be described. In the following description, "top" and "bottom" are used and defined in the drawings. However, the invention is not limited to such a directional definition.

Figure 4:
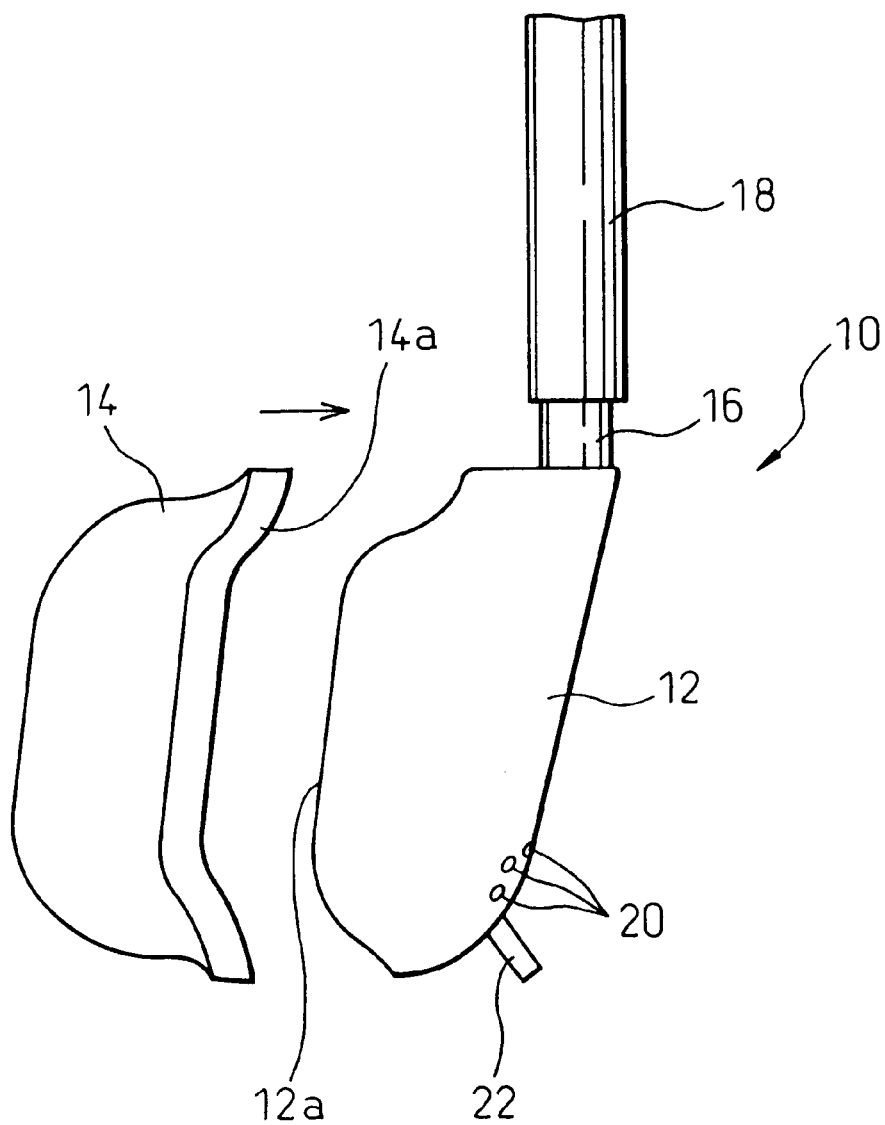
FIG. 4 is a exploded side view of the nasal mask of FIG. 1.

The nasal mask 10 includes a mask shell 12 and a flexible cushion 14 detachably attached to the mask shell 12 (FIG. 4). The mask shell 12 includes a pair of lugs 12a for a band for attaching the mask 10 to the face. The flexible cushion 14, in use, intimately contacts the face of the patient to provide a gas tight sealing between the face and the mask 10. The nasal mask 10 further includes a joint portion 16 which is provided at the top end of the mask shell 12 to define an air, inlet port of the mask shell 12. An air conduit 18 is connected to the joint portion 16 to direct air inside volume of the nasal mask 10 from an air source 24. The air source 24 supplies air alternately at a high inhalation pressure, for example at 20 cm $H_2O$, and at a low exhalation pressure, for example at 4 cm $H_2O$. The air supply cycle of the air source 24 can be determined to be at constant interval or to be controlled according to the breathing of the patient.

Figure 2:
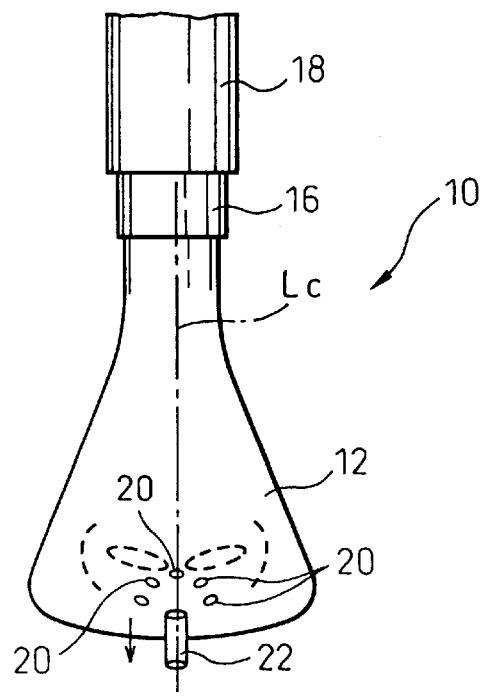
FIG. 2 is a front view of the nasal mask of FIG. 1.

The mask shell 12 includes at least an orifice 20, five orifices 20 being shown in FIG. 2, as an exhaust port provided in or adjacent to the bottom of the mask shell 12 close to the nose of the patient. A therapeutic gas inlet port 22 is provided on the mask shell 12 adjacent to the orifice 20. Preferably, in order to ensure the sufficient exhaust through the exhaust port 20, the exhaust port 20 has an opening area allowing outflow of at least 25 L/min under mask internal pressure of 18 $cmH_2O$. Further, in order to maintain the mask internal pressure for the intermittent positive pressure ventilation therapy, it is preferable that the exhaust port has an opening area allowing outflow of at most 50 L/min under a mask internal pressure of 18 $cmH_2O$.

Figure 3:
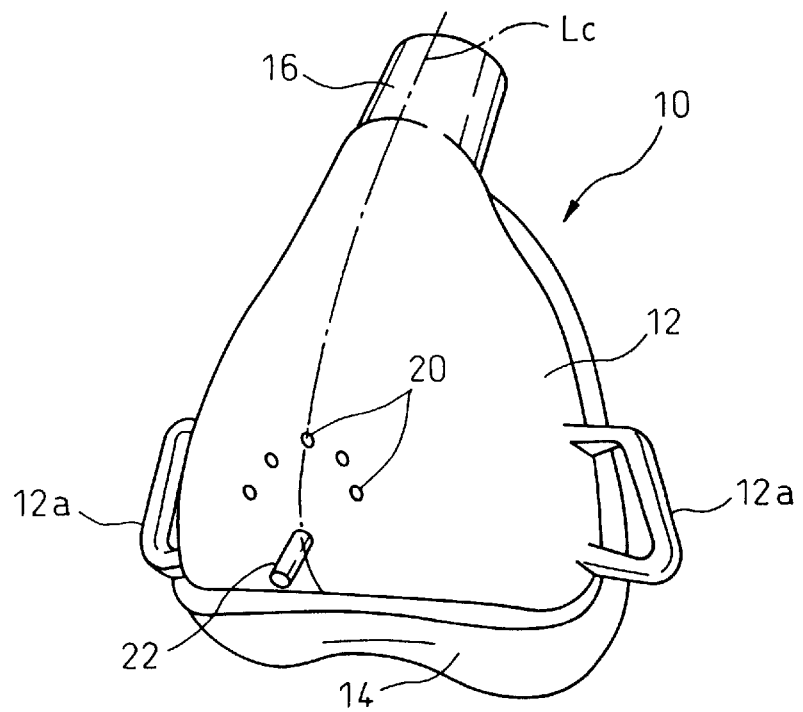
FIG. 3 is a perspective view of the nasal mask of FIG. 1.

Preferably, the air inlet defined by the joint portion 16, the exhaust port 20 and the therapeutic port 22 are disposed in order of precedence in the direction of the air flow through the air inlet port. Preferably, the air inlet port, the exhaust port and the therapeutic gas inlet port are substantially disposed in the symmetry plane or the center plane which includes the longitudinal axis of the face of the patient using the nasal mask 10. In this specification, the intersection between the symmetry plane and the mask shell 12 is referred to "center line Lc" (FIGS. 2 and 3). This arrangement prevents the excessive outflow of therapeutic gas through the exhaust port.

A therapeutic gas source 26 is fluidly connected to the therapeutic gas port 22 through a therapeutic gas conduit. In this embodiment, the therapeutic gas source 26 supplies, as an example, oxygen gas or oxygen concentrated gas at a constant flow rate to the nasal mask 10 as a therapeutic gas. The therapeutic gas inlet port 22 is upwardly oriented to direct the oxygen gas toward the upper portion of the inside volume of the mask shell 12, preferably toward a region Ro over the nose of the patient using this nasal mask 10. In another embodiment, the therapeutic gas may include nitrogen monoxide.

Figure 5:
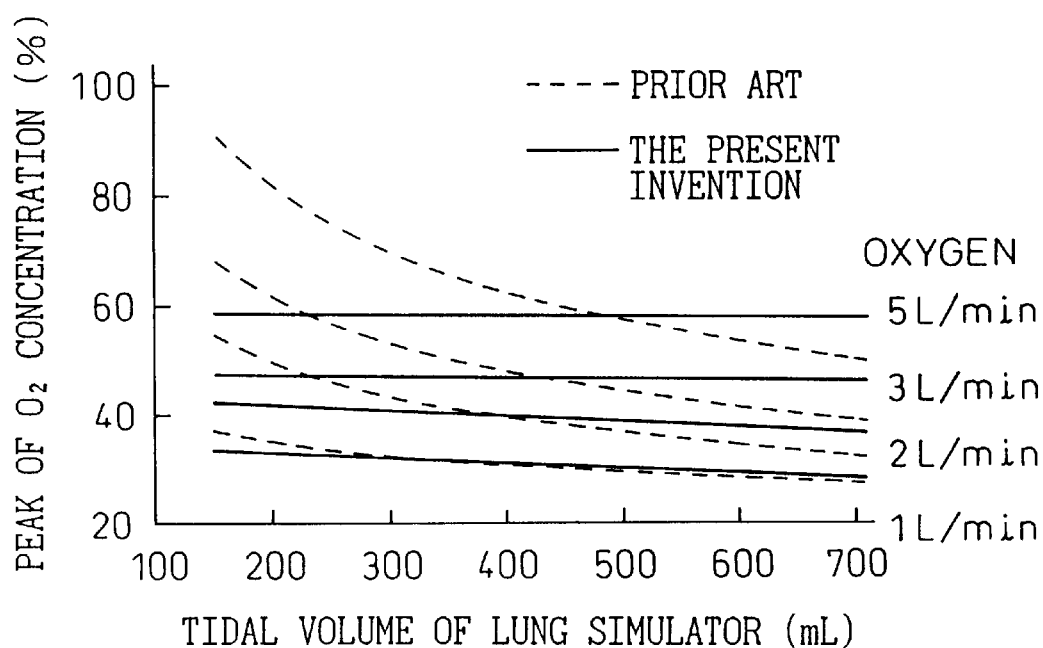
FIG. 5 is a graph of an experiment comparing the change of peak of oxygen concentration of inhalation gas between the prior art and the present invention.
Figure 6:
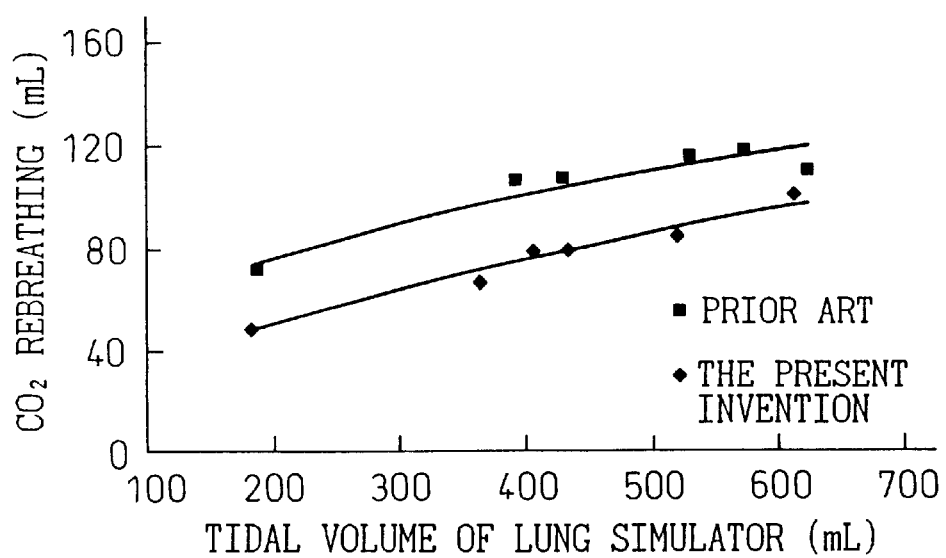
FIG. 6 is a graph of an experiment comparing the change of carbon dioxide rebreathing between the prior art and the present invention.

FIGS. 5 and 6 are experimental results of the nasal mask 10. The experiment was carried out to measure the peak of oxygen concentration in the inhalation and the volume of carbon dioxide rebreathing by using a lung simulator with the nasal mask 10 and the nasal mask of the prior art shown in FIG. 8. FIGS. 5 and 6 respectively show peak oxygen concentration and carbon dioxide rebreathing versus the tidal volume of the lung simulator.

Figure 8:
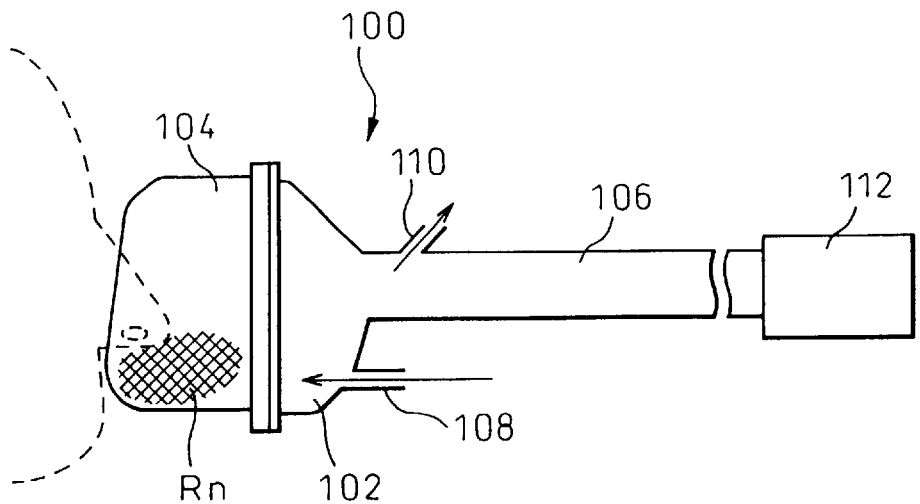
FIG. 8 is a schematic side view of a nasal mask of a prior art.

With reference to FIG. 5, with the nasal mask of the prior art of FIG. 8, the peak of oxygen concentration decreases with an increase in the tidal volume of the lung simulator. On the other hand, with the nasal mask 10 of this embodiment, the peak of the oxygen concentration is maintained substantially constant.

Figure 7:
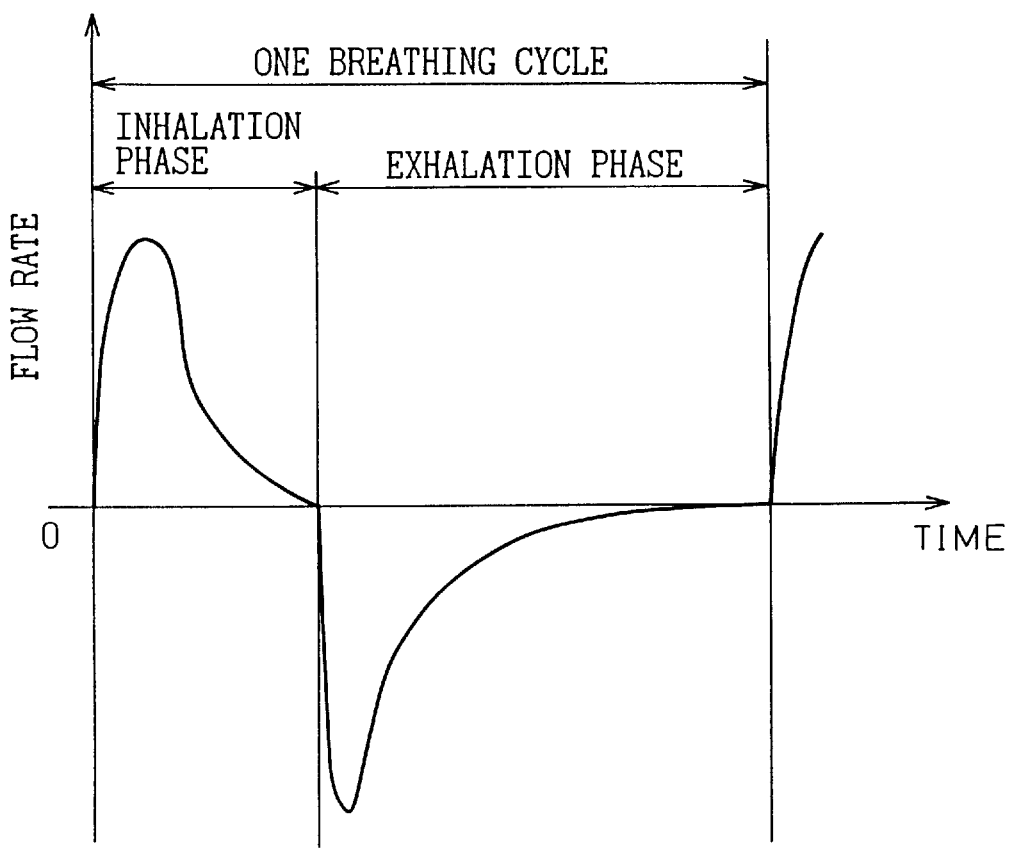
FIG. 7 is a graph of changes in flow rate of respiration.

With reference to FIG. 7, a typical breathing cycle is shown by a relation between the flow rate of the respiration and time. A breathing cycle includes inhalation and exhalation phases. In general, inhalation is carried out within a short time., and in particular, most of the inhalation gas is drawn in the front half of the inhalation phase. The exhalation phase is longer than the inhalation phase, in particular about twice as long, and most of the exhalation gas is discharged in the initial stage of the exhalation phase.

In case of the prior art, an oxygen rich space is produced in the region Rn under the nose (FIG. 8) in the end of the exhalation phase in which the flow rate of the exhalation gas is substantially zero. This oxygen rich space is drawn in in the initiation of the next inhalation phase.

On the other hand, in case of the present embodiment, the inflow of the oxygen through the therapeutic gas inlet port 22 penetrates the air flow through the air inlet port defined by the joint portion 16 to the upper portion of the inside volume of the nasal mask 10, in particular to the region Ro over the nose of the patient (FIG. 1) to produce the oxygen rich space there. It is assumed that the effects of exhalation flow from the nose and the air flow through the air inlet port against the flow condition within the region Ro over the nose is small. Therefore, the oxygen rich space is stably produced over the nose of the patient using the nasal mask 10 of the present embodiment. The volume of the oxygen rich space depends substantially on the flow rate of the oxygen gas through the therapeutic gas inlet port. The volume of the oxygen rich space produced over the nose changes the peak of the oxygen concentration of the inhalation gas. The larger the volume of the oxygen rich space, the higher the peak of the oxygen concentration of the inhalation observed. However, the volume is stable against changes in the flow rate of the exhalation gas from the patient.

Further, with the nasal mask 10 of the present embodiment, in the region Rn under the nose of the patient (FIG. 1) inside of the mask 10, a carbon dioxide rich space is produced. However, the volume of the carbon dioxide rich space is much smaller than that of the prior art of FIG. 8, since the exhaust port 20 is provided close to the nose to improve the exhaust efficiency of the exhalation gas from the nasal mask 10. This reduces carbon dioxide rebreathing as shown in FIG. 6.

With the mask 10 of the embodiment, the inhalation gas drawn into the lungs includes, in order of precedence, a carbon dioxide rich portion which originates from the carbon rich space under the nose, an oxygen rich portion which originates from the oxygen rich space over the nose, and a mixture of the air through the air inlet port and the oxygen through the therapeutic gas inlet port 22. The peak of the oxygen concentration measured by the above-described experiment corresponds to the oxygen concentration of the oxygen rich portion of the inhalation gas. At the initiation of an inhalation phase, some mixing action between the oxygen rich gas and the air flow through the air inlet port of the mask shell 12 is observed. However, it is assumed that the effect of the mixing is small and that the air flow through the air inlet port effectively pushes the oxygen rich space into the lungs with a high concentration of the oxygen maintained. This is the very advantageous effect of the invention since, in general, only the anterior portion of the inhalation flow can reach the effective portions of the lungs.

On the other hand, as described above, with the prior art nasal mask 100 of FIG. 8, the volume of the oxygen rich space is produced in the region Rn under the nose and strongly depends on the flow rate of the exhalation gas from the nose. Therefore, the peak of oxygen concentration of the inhalation strongly depends on the tidal volume of the lungs as shown in FIG. 5. The smaller the tidal volume of the lungs, the larger the volume of the oxygen rich space produced in the region Rn under the nose. Thus, the peak of the oxygen concentration increases with a decrease in the tidal volume as shown in FIG. 5. This is a problem when the patient sleeps and the tidal volume decreases, the oxygen concentration the inhalation gas increases, which results in depression of the respiratory center to decrease further the tidal volume.

The nasal mask disclosed in WO 98/34665 solves this problem. However, in the nasal mask of WO 98/34665, the oxygen is supplied into the air flow from the air source so that most of the supplied oxygen flows out through the exhaust port to increase the waste of oxygen. Further, an expansion effect of flow channel as the air-oxygen mixture flows inside of the mask shell from the air conduit promotes the mixing of air and oxygen to decrease the oxygen concentration. Therefore, the nasal mask of WO 98/34665 cannot maintain the peak oxygen concentration in the inhaled gas as much as the nasal mask 10 of the present invention.

It will also be understood by those skilled in the art that the forgoing description is a preferred embodiment of the disclosed device and that various changes and modifications may be made without departing from the spirit and scope of the invention.

We claim:

1. A nasal mask for use with a system for supplying air, with a therapeutic gas, to the airways of a patient, comprising:

a mask shell adapted to be put over the nose of the patient using the nasal mask, the mask shell having an inside volume;

an air inlet port that supplies air to the inside volume from an air source;

an exhaust port, provided in the mask shell, for discharging the patient's exhalation gas to atmosphere; and a therapeutic gas inlet port, provided on the mask shell adjacent to the exhaust port, the therapeutic gas inlet port being fluidly connected to a therapeutic gas source that supplies a therapeutic gas to the inside volume of the mask shell at a constant flow rate, the therapeutic gas inlet port being oriented toward a portion of the inside volume of the nasal mask over the nose of the patient using the nasal mask;

wherein the air inlet port, the exhaust port and the therapeutic gas inlet port are disposed in that order, in the direction of air flow through the air inlet port along the center line of the mask shell.

2. A nasal mask according to claim 1 further comprising a flexible cushion detachably attached to the mask shell, the flexible cushion, in use, intimately contacting the face of the patient to provide a gas tight sealing between the face and the mask shell.

3. A nasal mask according to claim 1 wherein the exhaust port has an opening area allowing outflow of at least 25 L/min under mask internal pressure of 18 $cmH_2O$.

4. A nasal mask according to claim 1 wherein the exhaust port has an opening area allowing outflow of at most 50 L/min under mask internal pressure of 18 $cmH_2O$.

5. A nasal mask according to claim 1 wherein the therapeutic gas includes oxygen gas.

6. A nasal mask according to claim 1, wherein the therapeutic gas inlet port is adjacent to the exhaust port, so as to be relatively closer to the exhaust port than to the air inlet port.

* * * * *